(12) United States Patent
Falchi et al.

(10) Patent No.: US 8,344,136 B2
(45) Date of Patent: Jan. 1, 2013

(54) PROCESS FOR THE PREPARATION OF BRINZOLAMIDE

(75) Inventors: Alessandro Falchi, Sassari (IT);
Ottorino De Lucchi, Padua (IT);
Andrea Castellin, Padua (IT)

(73) Assignee: PHF S.A., Lugano (CH)

( * ) Notice: Subject to any disclaimer, the term of this patent is extended or adjusted under 35 U.S.C. 154(b) by 104 days.

(21) Appl. No.: 12/999,054

(22) PCT Filed: Jun. 15, 2009

(86) PCT No.: PCT/IB2009/052538
§ 371 (c)(1),
(2), (4) Date: Jan. 10, 2011

(87) PCT Pub. No.: WO2010/004457
PCT Pub. Date: Jan. 14, 2010

(65) Prior Publication Data
US 2011/0118461 A1     May 19, 2011

(30) Foreign Application Priority Data

Jun. 16, 2008 (IT) .............................. MI2008A1084

(51) Int. Cl.
*C07D 513/20* (2006.01)
*C07D 513/04* (2006.01)
*C07D 333/34* (2006.01)
(52) U.S. Cl. .......................................... 544/48; 544/63
(58) Field of Classification Search ..................... 544/48
See application file for complete search history.

(56) References Cited

U.S. PATENT DOCUMENTS

| 5,240,923 A | 8/1993 | Dean et al. |
| 5,470,973 A | 11/1995 | Hoff |
| 5,585,377 A | 12/1996 | Dean et al. |

FOREIGN PATENT DOCUMENTS

WO      WO 92/16525 A1   10/1992

*Primary Examiner* — Kahsay T Habte
(74) *Attorney, Agent, or Firm* — Dickstein Shapiro LLP

(57) ABSTRACT

The present invention relates to a process for the preparation of Brinzolamide, or 2H-thieno[3,2-e]-1,2-thiazin-6-sulfonamide, 4-(ethyl amino)-3,4-dihydro-2-(3-methoxypropyl)-, 1,1-dioxide, (4R)-via intermediates 2,3-dihydro-4H-thieno[3,2-e]-1,2-thiazin-4-ones, 1,1-dioxide. Further objects of the present invention are the intermediates mentioned above and other intermediates of the synthesis.

12 Claims, No Drawings

PROCESS FOR THE PREPARATION OF BRINZOLAMIDE

FIELD OF THE INVENTION

The present invention relates to a process for the preparation of Brinzolamide, or 2H-thieno[3,2-e]-1,2-thiazin-6-sulfonamide, 4-(ethyl amino)-3,4-dihydro-2-(3-methoxypropyl)-, 1,1-dioxide, (4R)- via intermediates 2,3-dihydro-4H-thieno[3,2-e]-1,2-thiazin-4-ones, 1,1-dioxide. Further objects of the present invention are the intermediates mentioned above and other intermediates of the synthesis.

BACKGROUND ART

Brinzolamide is a carbonic anhydrase II inhibitor, used to lower intraocular pressure and glaucoma. It is sold by Alcon under the name of Azopt, as 1% ophthalmic suspension.

EP 527801 claims Brinzolamide and describes a process to prepare it in 14 steps starting from 3-acetylthiophene (scheme 1). It is a synthesis typical of medicinal chemistry not applicable at industrial level, for which no specific preparations are described, because Brinzolamide is not among the preferred compounds of the invention.

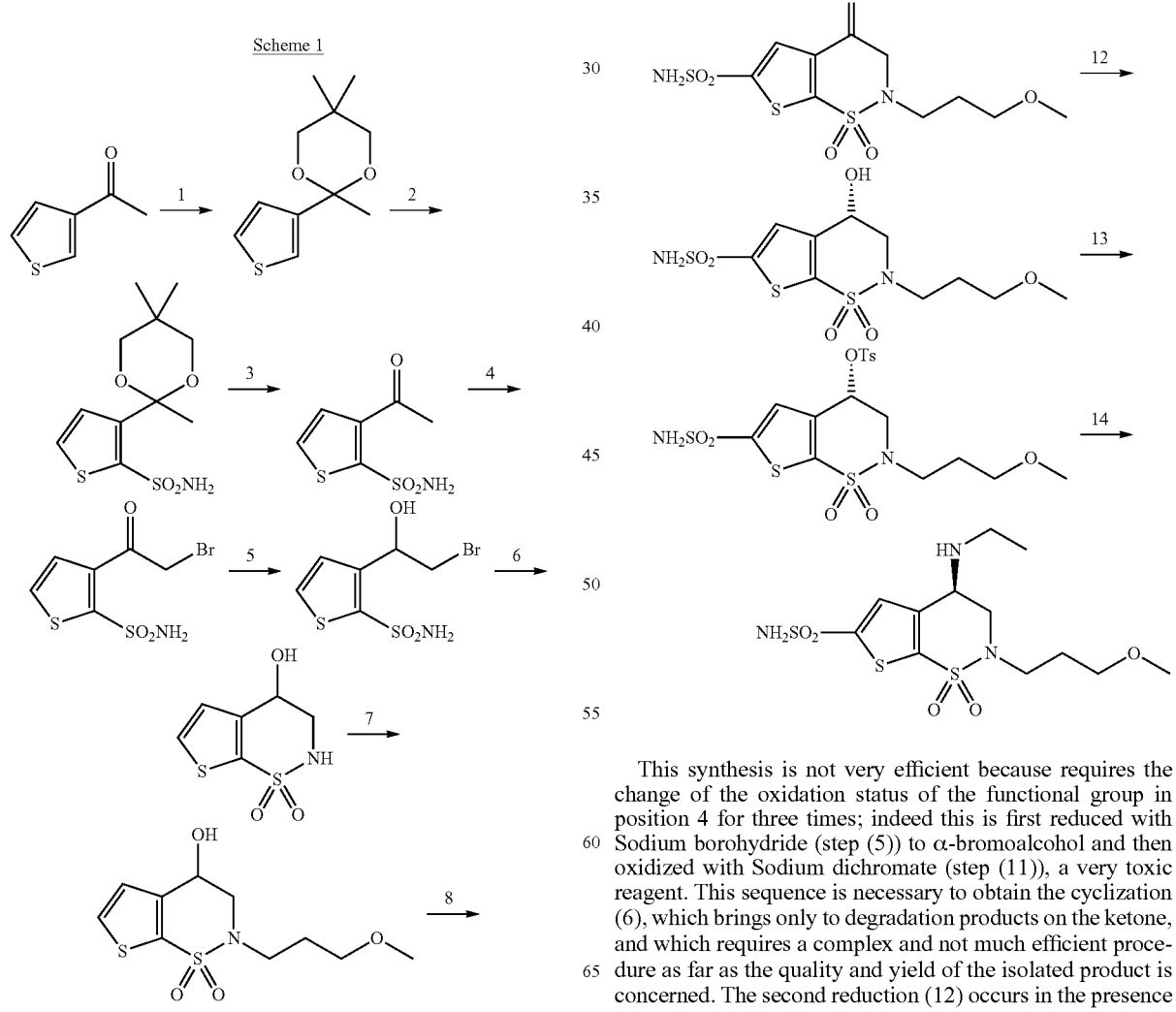

Scheme 1

This synthesis is not very efficient because requires the change of the oxidation status of the functional group in position 4 for three times; indeed this is first reduced with Sodium borohydride (step (5)) to α-bromoalcohol and then oxidized with Sodium dichromate (step (11)), a very toxic reagent. This sequence is necessary to obtain the cyclization (6), which brings only to degradation products on the ketone, and which requires a complex and not much efficient procedure as far as the quality and yield of the isolated product is concerned. The second reduction (12) occurs in the presence of (+)-β-chlorodiisopinocamphenylborane, an expensive enantioselective reducing agent, with a stoichiometric excess of 5:1, which requires reaction conditions not easily achievable at industrial scale (3 days of reaction at −22° C., difficult work up and chromatography) to isolate the product.

It can be inferred from the patent that there is the possibility to fix the stereogenic centre through selective crystallization of the salt of a chiral acid as di-p-toluoyl-D-tartaric acid, expensive resolution agent, with consequent loss of at least half of the substrate.

EP 617038 describes a process for the preparation of Brinzolamide and its analogues starting from 3-acetyl-2,5-dichlorothiophene (scheme 2).

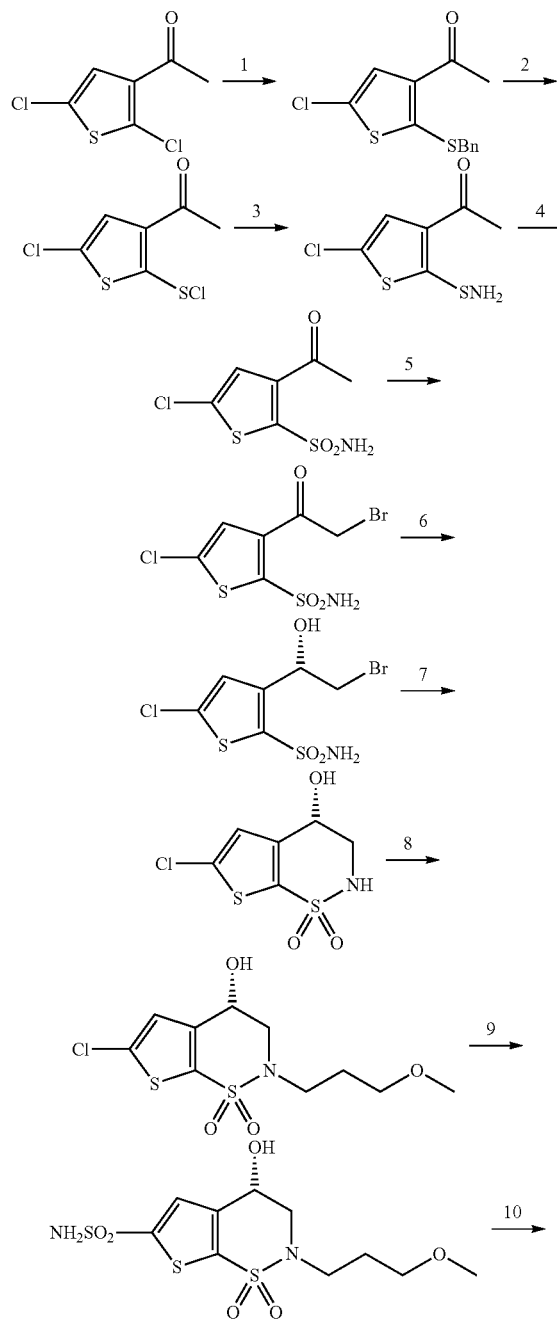

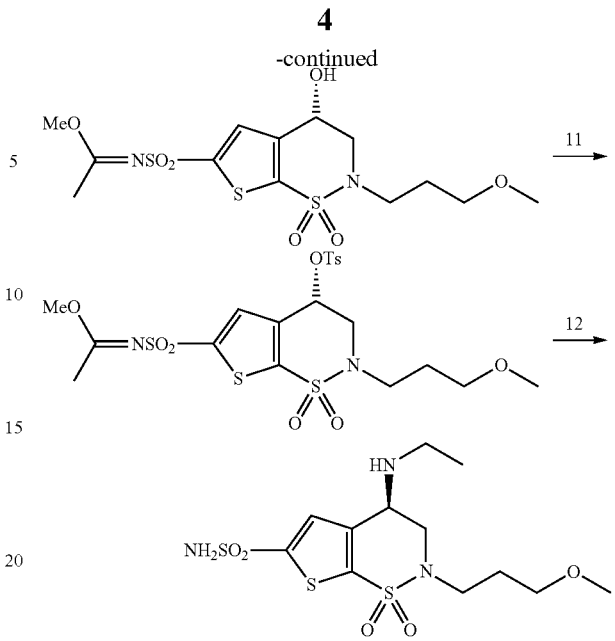

The reduction (6) with (+)-β-chlorodiisopinocamphenylborane and the cyclization (7) bring to the optically active alcohol 2H-thieno[3,2-e]-1,2-thiazin-4-ol, 6-chloro-3,4-dihydro-, 1,1-dioxide, (4S)-. The formation of a product enriched with one of the enantiomer is too early in the synthesis, with a consequent risk of racemisation during the following steps, while the reduction would be more efficient if performed on a more advanced intermediate. The disadvantages of the use of the enantioselective reducing agent (6) and of the cyclization of the alcohol (7) are the same of the method described in Scheme 1. Another disadvantage is the alkylation (8) with 1-bromo-3-methoxypropane, that, in order to avoid the reaction of the oxydrilic group, is performed portionwise, with low temperatures and long reaction times.

The sulfonamide is introduced in position 6 through metallation with n-butyl lithium, an expensive raw material, and then with a reaction with sulphurous anhydride and hydroxylamino-O-sulphonic acid. The base should be used in substantial excess (2,3 eq.), because the oxydrilic group reacts with the first equivalent. In this case the protection of the oxydrilic group as described in Scheme 1 is not possible without running the risk of racemization of the substrate.

Lastly, the conversion of the secondary alcohol to the amine is difficult and requires the protection (10) of the primary sulfonamide with trimethyl orthoacetate, the activation (11) of the oxydrilic group with tosyl chloride and finally the substitution (12) of the tosyl group with ethylamine and at the same time the aminolysis of the protection of sulfonamide with the excess of ethylamine.

This synthesis is described in *Org. Process Res. Dev.* 3, 1999, 114, written by the R&D laboratories of Alcon. So it is reasonable to believe that this synthesis is used by Alcon at industrial level. Anyway, due to the low purity of the product obtained (97%), several crystallizations are needed to have a product of acceptable pharmaceutical grade.

U.S. Pat. No. 5,470,973 describes a variant of the synthesis in scheme 1, which involves an alternative preparation of the syntone 2H-thieno[3,2-e]-1,2-thiazin-4-ol, 6-chloro-3,4-dihydro-2-(3-methoxypropyl)-, 1,1-dioxide, (4S)- and the other analogues lacking chlorine in position 6 or the 3-methoxypropylic chain (scheme 3).

Scheme 3

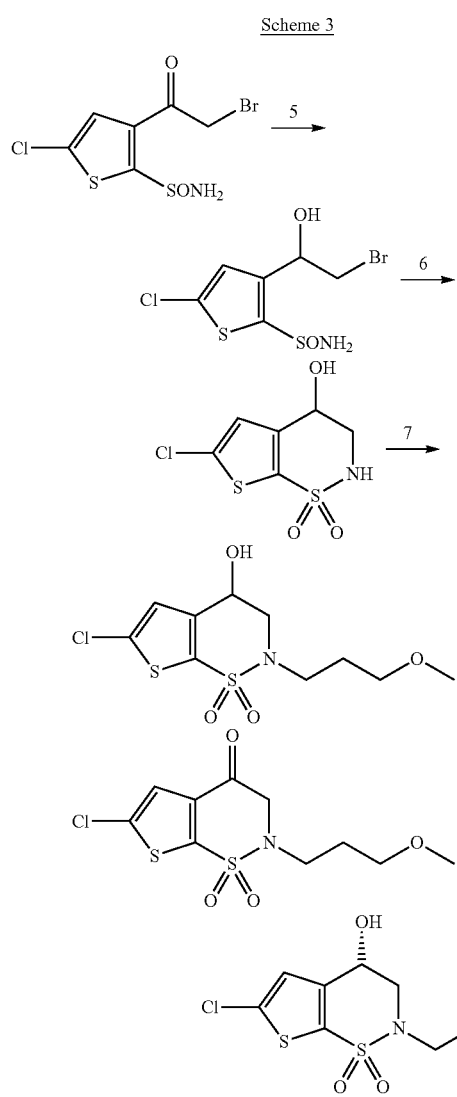

To introduce the chiral centre, firstly the oxidation (8) with dichromate is performed, and then the stereoselective reduction (9) with (S)-tetrahydro-1-methyl-3,3-diphenyl-1H,3H-pyrrol[1,2-c][1,3,2]oxazaborole are performed. The need of oxidizing first and then reducing was already commented in the description of the first synthetic path; the low enantiomeric excess (92%) is another disadvantage.

So it is evident the need of an alternative process for the preparation of Brinzolamide which can resolve the above mentioned technical problems.

BRIEF DESCRIPTION OF THE INVENTION

The present invention describes a process for the preparation of compounds 2,3-dihydro-4H-thieno[3,2-e]-1,2-thiazin-4-ones, 1,1 dioxide and their conversion to Brinzolamide. Further objects of the present invention are the above mentioned intermediates, intermediates 3-[2-(halomethyl)-1,3-dioxolan-2-yl]thiophene-2-sulfonamide and 3-[2-(sulphonylmethyl)-1,3-dioxolan-2-yl]thiophene-2-sulfonamide and intermediates 2',3'-dihydrospiro[1,3-dioxolan-2,4'-thieno[3,2-e][1,2]thiazine], 1',1'-dioxide.

DETAILED DESCRIPTION OF THE INVENTION

It was surprisingly found a process for the preparation of compounds with structure 1

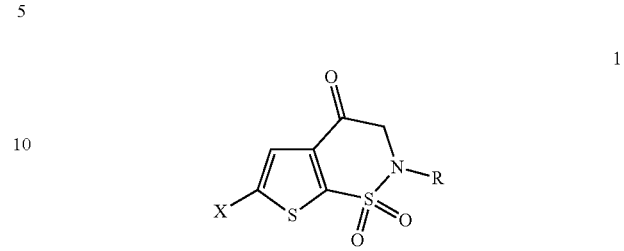

where X can be hydrogen, halogen, thiol, thioether, or amide or halogenide of sulphonic acid,
R can be hydrogen, alkyl, alkoxy alkyl, haloalkyl, aryl or aryl alkyl,
including the steps of
a) reaction of a compound of formula 2

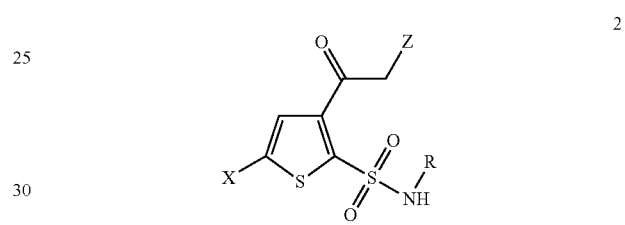

wherein X and R have the same meaning as above and Z can be a halogen or a sulphonic esther,
with an alcohol or a diol to give a ketal of formula 3

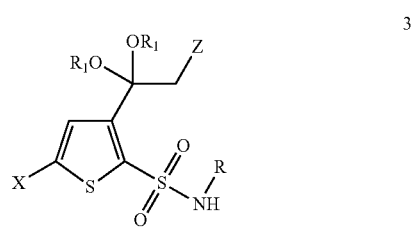

wherein X, R and Z have the same meaning as above and $R_1$ is an alkyl, linear or branched, or aryl alkyl, and the two groups $R_1$ can be separated or joined together to form a cycle,
b) cyclization of the compound of formula 3 to form a compound of formula 4

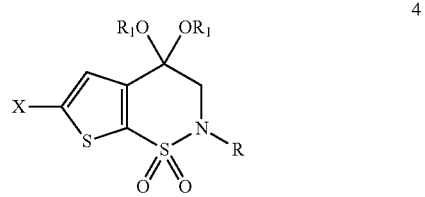

wherein X, R and $R_1$ have the same meaning as above,
c) hydrolysis of a compound of formula 4.
X is preferably hydrogen, chlorine, bromine, sulfonamide;
R is preferably hydrogen, 3-chloropropyl, 3-bromopropyl, 3-iodopropile o 3-methoxypropyl, preferably 3-methoxypropyl;

X is preferably chlorine or bromine, more preferably bromine;

R₁ is preferably methyl, ethyl, isopropyl, t-butyl, benzyl, or a chain formed by ethylene, propylene, 2,2-dimethylpropylene, more preferably ethylene.

The protection a) of ketone 2 with an appropriate alcohol or diol is preferably performed in a highly boiling solvent such as toluene or xylene, in the presence of an acidic catalyst, preferably chosen among p-toluensulphonic acid, sulphuric acid and boron trifluoride etherate, at a temperature suitable to remove by distillation the water generated during the process.

Cyclization b) is performed preferably in the presence of a base to activate the sulphonamidic group and to neutralize the acid generated during the reaction; this base is preferably chosen among potassium carbonate, sodium carbonate, triethylamine, pyridine, potassium hydroxide, sodium hydroxide, sodium hydride, more preferably is potassium carbonate. The reaction is performed in a solvent preferably chosen among dimethylsulphoxide, dimethylformamide, N-methylpyrrolidone, or their mixture with THF, toluene and other apolar solvents, more preferably in dimethylsulphoxide, preferably at a temperature between 20° C. and 80° C. In the preferred conditions the reaction takes place in less than one hour.

The hydrolysis c) of the ketal to carbonyl is preferably performed with an acidic catalyst, preferably with hydrochloric acid, sulphuric acid, hydrobromic acid, more preferably with aqueous hydrochloric acid, in the presence of water and an organic solvent preferably chosen among toluene, acetone, ethanol, methanol, THF, more preferably toluene, preferably at a temperature between 0° C. and 80° C. In the preferred conditions the reaction takes place in 8 hours.

The invention includes an optional step of transformation of the group X in a group X with a different meaning and/or the transformation of the group R in a group R with a different meaning after one of the steps a), b) or c), or on the open ketale 3, on the cyclised ketal 4 or on the ketone 1.

When in the compounds of formula 3 or 4 X is hydrogen or chlorine, this can be efficiently transformed in sulphonamide or one of its synthetic precursors according to what is described in *Organic Process Research & Development* 1999, 3, 114-120 or *J. Org. Chem.* 1997, 62, 9372-9375, or *J. Org. Chem.* 1993, 58, 1672-1679, or *J. Org. Chem.* 1991, 56, 763-769. The process object of this invention is advantageous because it allows to insert a sulphonamidic functional group using a stoichiometric quantity of butyl lithium, without having this reacting with the carbonylic group, protected under a ketal form.

When in the compounds of formula 3 or 4 R is hydrogen, this can be transformed in alkyl, alkoxy alkyl, haloalkyl, aryl or aryl alkyl after a reaction with an alkyl halide, a sulphate or a sulphonate, preferably after a reaction with 1,3-dichloropropane, 1,3-dibromopropane, 1,3-diiodopropane, 1-chloro-3-methoxypropane or 1-bromo-3-methoxypropane, more preferably with 1-chloro-3-methoxypropane or 1-bromo-3-methoxypropane. This procedure is advantageous because it allows to insert an alkyl, alkoxy alkyl, aryl or aryl alkyl group, preferably 3-chloropropyl, 3-bromopropyl, 3-iodopropyl o 3-methoxypropyl, more preferably 3-methoxypropyl, in the same conditions of the cyclization reaction of step b).

When in the compounds of formula 3 or 4 R is 3-chloropropyl, 3-bromopropyl, 3-iodopropyl, this can be transformed in 3-methoxypropyl after a reaction with sodium or potassium methylate, or with methanol in the presence of a strong base.

A particularly preferred embodiment of the invention is a process for the preparation of 2-(3-methoxypropyl)-4-oxo-3,4-dihydro-2H-thieno[3,2-e][1,2]thiazine, 1,1-dioxide of formula 5

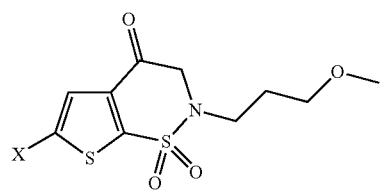

wherein X is hydrogen, chlorine, or sulphonamide, comprising the steps of a) Reaction of the compound of formula 6

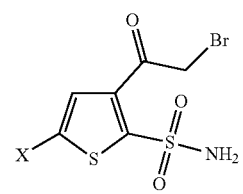

wherein X is hydrogen or chlorine, with ethylene glycol in the presence of an acid, to obtain the compound 7

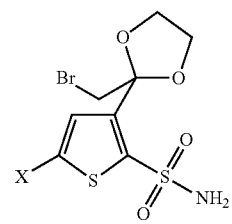

wherein X is hydrogen or chlorine, b1) Cyclization of the compound of formula 7 in the presence of a base to obtain the compound of formula 8

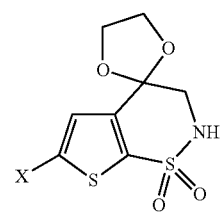

wherein X is hydrogen or chlorine;

b2) Reaction of the compound of formula 8 with 1-chloro-3-methoxypropane or 1-bromo-3-methoxypropane to obtain the compound of formula 9

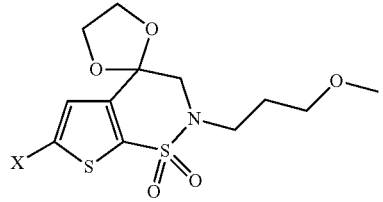

9 wherein X is hydrogen or chlorine;

b3) Optional conversion of the group X in a sulphonamide;

c) Hydrolysis of the compound of formula 9, wherein X is sulphonamide, hydrogen or chlorine.

Step b3) of conversion of the group X in sulphonamide can be performed on the compounds of formula 8 where X is hydrogen or chlorine and is preferably performed with a reaction with butyl lithium in tetrahydrofuran at −40° C., followed by bubbling of sulphurous anhydride in the solution until an acid pH is achieved, removal of the solvent and addition of hydroxylamino-O-sulphonic acid in water in the presence of sodium acetate.

Starting from the compounds of formula 1 it is possible to prepare Brinzolamide by reducing the carbonyl group to an alcohol and then resolving the enantiomers (see EP 527801), or reducing enantioselectively the carbonyl group to an alcohol by using a chemical or enzymatic catalysis (see EP 527801, EP 617038 and U.S. Pat. No. 5,470,973), or through the formation of the corresponding ketimine followed by its reduction with a non enantioselective reducing agent followed by its resolution, or by reducing enantioselectively the ketimine through chemical or enzymatic catalysis. These reactions can provide the transformation of groups X and R in different groups, for example to have them protected or to activate them to the above mentioned reactions.

It is further object of this invention a process for the preparation of Brinzolamide including the process for the preparation of compounds with the above mentioned formula 1 and one or more of the following reactions:

i. Reduction of the carbonyl in position 4 to an alcohol;
ii. Stereoselective reduction of the carbonyl in position 4 to an alcohol;
iii. Transformation of the alcohol in position 4 obtained at i and ii in halogenide or sulphonic esther;
iv. Substitution of the halogenide or sulphonic esther obtained at iii with an amine, preferably ethylamine;
v. Reaction of the ketone with an amine, preferably ethylamine, to form the ketimine in position 4;
vi. Reduction of the ketimine in position 4 obtained at v to amine;
vii. Stereoselective reduction of the ketimine in position 4;
viii. Transformation of the group X in a group X with a different meaning;
ix. Transformation of the group R in a group R with a different meaning.
x. Resolution of the racemate.

Further object of the present invention are the compounds chosen in the group consisting of the compounds of formula 3

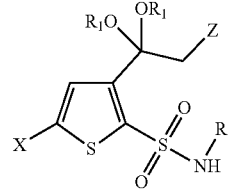

3 wherein X is hydrogen, halogen, thiol, thioether, or amide or halogenide of sulphonic acid, R is hydrogen, alkyl, alkoxy alkyl, haloalkyl, aryl or aryl alkyl;

Z is a halogen or sulphonic esther;

$R_1$ is an alkyl, linear o branched, or aryl alkyl, and the two groups $R_1$ can be separated or joined together to form a cycle; of the compounds of formula 4

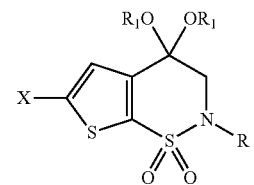

4 wherein X, R and $R_1$ have the above mentioned meaning; and of the compounds of formula 1

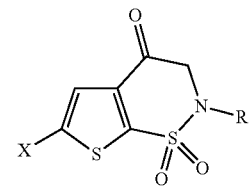

1 wherein X and R have the above mentioned meaning, provided that in the compounds of formula 1 when X is hydrogen or chlorine, R is not hydrogen or 3-methoxypropyl and when X is sulphonamide, R is not 3-methoxypropyl. These compounds are useful intermediates in the present process for the preparation of Brinzolamide.

Finally the present invention describes a simple method for the preparation of Brinzolamide and the compounds of formula 1 with the following advantages:

1) The protection a) of the carbonyl activates the reaction of intramolecular cyclization b);
2) The protection a) of the carbonyl allows to perform the transformation of groups X and R (for example changing X=Cl or H in X=$SO_2NH_2$) without involving the first functional group;
3) The process uses cheap raw materials, commercially available or easily synthesized,
4) All the reactions have high yields and can be easily transferred at industrial scale.

Other characteristics and advantages of the inventive process will be highlighted in the following description of the preferred examples of the synthesis, which are indicative and not limited to these ones.

EXAMPLES

General Procedure 1

Protection of the Carbonylic Group

The compound of formula 2 is suspended in toluene (10-20 volumes) and ethylene glycol (5-10 equivalents); p-toluensulphonic acid is added in catalytical quantity. The mixture is heated until reflux with azeotropic removal of water for 5-12 hours, until complete conversion (HPLC). At the end of the reaction the solution is cooled down at room temperature. Triethylamine and water are added (at least double compared with glycol) and the phases are separated. The organic phase is washed with water and concentrated under vacuum to give the desired product 7 as a light-colored solid with HPLC purity above 95% and with a yield of 80-95%.

Example 1

3-[2-(bromomethyl)-1,3-dioxolan-2-yl]thiophene-2-sulphonammide 7 (X=hydrogen)

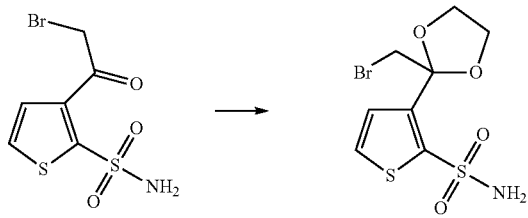 [SMILES: NS(=O)(=O)c1sccc1C(=O)CBr ; NS(=O)(=O)c1sccc1C1(CBr)OCCO1]

The desired compound is prepared according to general procedure 1 starting from 3-(bromoacetyl)thiophene-2-sulphonammide with a yield of 87%.

$^1$H-NMR (300 MHz, DMSO-$d_6$): 7.63 (d, 1H), 7.32 (s, 2H), 7.12 (d, 1H), 4.10 (m, 2H), 3.96 (s, 2H), 3.86 (m, 2H).

LC-MS: [M+H]$^+$=328.

Example 2

3-[2-(bromomethyl)-1,3-dioxolan-2-yl]-5-chlorothiophene-2-sulphonamide 7 (X=chlorine)

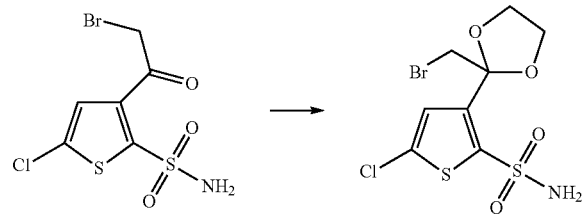 [SMILES: NS(=O)(=O)c1sc(Cl)cc1C(=O)CBr ; NS(=O)(=O)c1sc(Cl)cc1C1(CBr)OCCO1]

The desired compound is prepared according to general procedure 1 starting from 3-(bromoacetyl)-5-chlorothiophene-2-sulphonamide with a yield of 93%.

$^1$H-NMR (300 MHz, DMSO-$d_6$): 7.55 (s, 2H), 7.14 (s, 1H), 4.09 (m, 2H), 3.94 (s, 2H), 3.88 (m, 2H).

GC-MS: [M]$^{+\cdot}$=363.

General Procedure 2

Intramolecular Cyclization

The compound of structure 3 is dissolved in DMSO (5-10 volumes); potassium carbonate is added (1.2-2.5 equivalents) and the mixture is heated to 50-60° C. for one hour. At the end of the conversion it is recovered with water and ethyl acetate and the aqueous phase is acidified until a pH=6-7. The phases are separated and the organic phase is washed with water. The product 8 is isolated through distillation of the solvent under vacuum, abtaining a solid with a HPLC purity of 80-95% and a yield of 90-97%.

Example 3

2',3'-dihydrospiro[1,3-dioxolan-2,4'-thieno[3,2-e][1,2]thiazine], 1',1'-dioxide 8 (X=hydrogen)

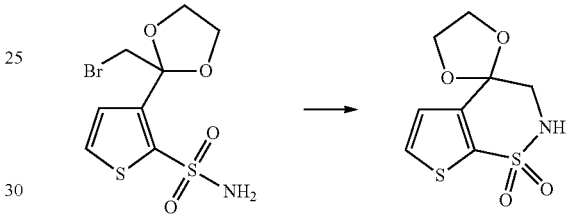

The desired compound is prepared according to general procedure 2 starting from 3-[2-(bromomethyl)-1,3-dioxolan-2-yl]thiophene-2-sulphonamide of example 1 with a yield of 90%.

$^1$H-NMR (300 MHz, DMSO-$d_6$): 8.69 (t, 1H), 7.89 (d, 1H), 7.18 (d, 1H), 4.17 (m, 2H), 4.06 (m, 2H), 3.54 (d, 2H).

LC-MS: [M+H]$^+$=248.

Example 4

6'-chloro-2',3'-dihydrospiro[1,3-dioxolan-2,4'-thieno[3,2-e][1,2]thiazine], 1',1'-dioxide 8 (X=chlorine)

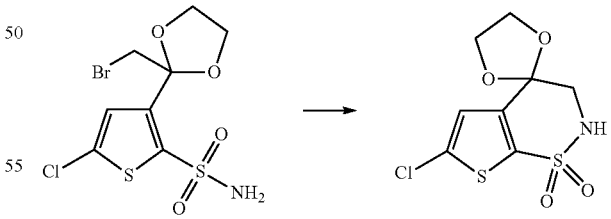

The desired compound is prepared according to general procedure 2 starting from 3-[2-(bromomethyl)-1,3-dioxolan-2-yl]-5-chlorothiophen-2-sulphonammide of example 2 with a yield of 97%.

$^1$H-NMR (300 MHz, DMSO-$d_6$): 8.91 (t, 1H), 7.34 (s, 1H), 4.17 (m, 2H), 4.04 (m, 2H), 3.56 (d, 2H).

LC-MS: [M+H]$^+$=282

GC-MS: [M]$^{+\cdot}$=281..

General Procedure 3

Cyclization Followed by Alkylation of Sulphonamide

The compound of structure 3 is dissolved in DMSO (5-10 volumes); potassium carbonate is added (1.2-2.5 equivalents) and the mixture is heated for one hour at 50-60° C. When the conversion is complete, 1-chloro-3-methoxypropane (1.5-3 equivalents) is added to the suspension and the mixture is heated again at 60° C. for 2-8 hours.

When the conversion is complete, the mixture is recovered with water and toluene. The phases are separated and the organic phase is washed with water. The product 9 is isolated through distillation of the solvent under vacuum, obtaining a solid with a HPLC assay of 85-95% and a yield of 90-99%.

Example 5

2'-(3-methoxypropyl)-2',3'-dihydrospiro[1,3-dioxolan-2,4'-thieno[3,2-e][1,2]thiazin], 1',1'-dioxide 9 (X=hydrogen)

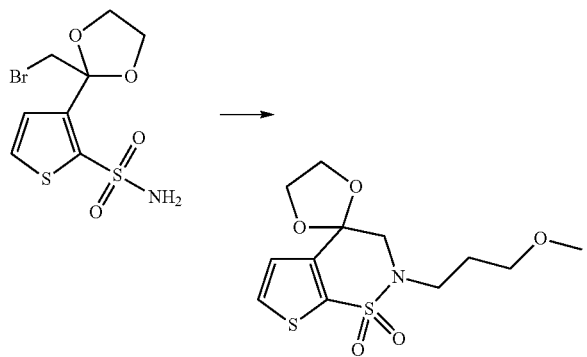

The desired compound is prepared according to the general procedure 3 starting from 3-[2-(bromomethyl)-1,3-dioxolan-2-yl]thiophene-2-sulphonamide of example 1 with a yield of 90%.

$^1$H-NMR (300 MHz, DMSO-$d_6$): 7.94 (d, 1H), 7.22 (d, 1H), 4.17 (m, 2H), 4.07 (m, 2H), 3.81 (s, 2H), 3.4-3.3 (m, 4H), 3.21 (s, 3H), 1.81 (m, 2H).

LC-MS: [M+H]$^+$=320.

Example 6

6'-chloro-2'-(3-methoxypropyl)-2',3'-dihydrospiro[1,3-dioxolan-2,4'-thieno[3,2-e][1,2]thiazin], 1',1'-dioxide 9 (X=chlorine)

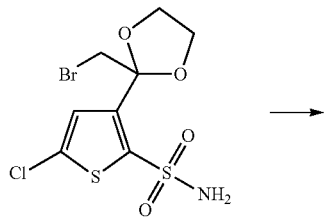

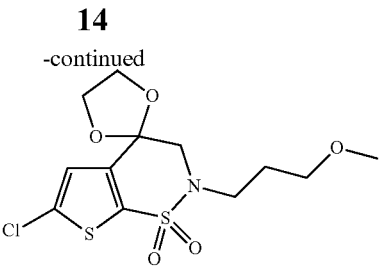

The desired compound is prepared according to general procedure 3 starting from 3-[2-(bromomethyl)-1,3-dioxolan-2-yl]-5-chlorothiofen-2-sulphonamide of example 2 with a yield of 99%.

$^1$H-NMR (300 MHz, DMSO-$d_6$): 7.40 (s, 1H), 4.19 (m, 2H), 4.06 (m, 2H), 3.83 (s, 2H), 3.4-3.3 (m, 4H), 3.20 (s, 3H), 1.81 (m, 2H).

LC-MS: [M+H]$^+$=354.

General Procedure 4

Introduction of the Second Sulphonamidic Group

The compound of formula 4 is dissolved under Nitrogen in tetrahydrofuran (10-20 volumes) and cooled at −40° C. n-butyllithium in heptane solution (1.2-3 eq) is added dropwise and it is left under stirring for 1 hour. Anhydrous sulphurous anhydride is added to the solution kept at −40° C. until a sample of the solution, quenched with water, has a pH=4-5. The suspension is stirred allowing the temperature to increase slowly, then the solvent is concentrated under vacuum; the solid is dissolved in water and the aqueous phase is washed with methylene chloride. The aqueous phase is added to an aqueous solution of sodium acetate (6-8 equivalents) and hydroxylamino-O-sulphonic acid (2-4 equivalents) and stirred at room temperature for 2-8 hours. When the conversion is complete ethyl acetate is added and the phases are separated. The organic phase is washed with a solution of bicarbonate and water. The product 9 with X=sulphonamide is isolated through distillation of the solvent under vacuum, obtaining a solid with a HPLC assay of 90-95% and a yield of 75-90%.

Example 7

2'-(3-methoxypropyl)-2',3'-dihydrospiro[1,3-dioxolan-2,4'-thieno[3,2-e][1,2]thiazin]-6'-sulphonamide, 1',1'-dioxide 9 (X=sulphonamide)

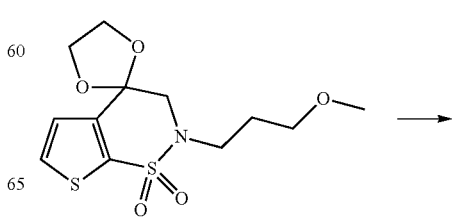

-continued

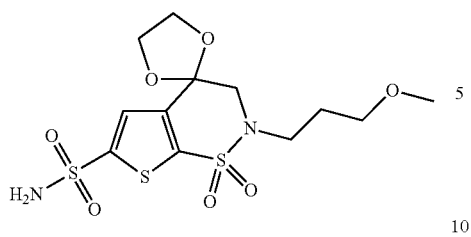

The desired compound is prepared according to general procedure 4 starting from 2'-(3-methoxypropyl)-2',3'-dihydrospiro[1,3-dioxolan-2,4'-thieno[3,2-e][1,2]thiazin], 1',1'-dioxide of example 5 with a yield of 76%.

$^1$H-NMR (300 MHz, DMSO-d$_6$): 8.05 (s, 2H), 7.59 (s, 1H), 4.16 (m, 2H), 4.07 (m, 2H), 3.87 (s, 2H), 3.4-3.3 (m, 4H), 3.21 (s, 3H), 1.81 (m, 2H).

LC-MS: [M+H]$^+$=399.

Example 8

2'-(3-methoxypropyl)-2',3'-dihydrospiro[1,3-dioxolan-2,4'-thieno[3,2-e][1,2]thiazin]-6'-sulphonamide, 1',1'-dioxide 9 (X=sulphonamide)

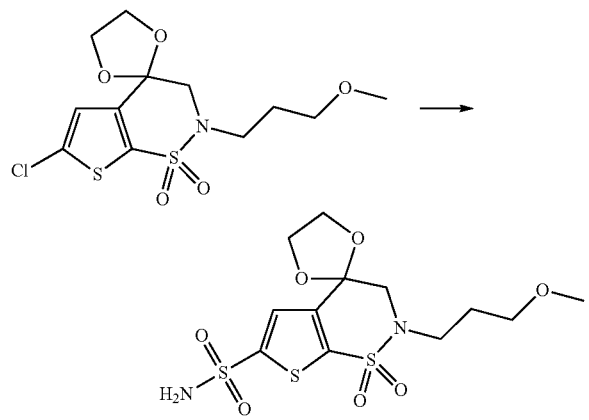

The desired compound is prepared according to general procedure 4 starting from 6'-chloro-2'-(3-methoxypropyl)-2',3'-dihydrospiro[1,3-dioxolan-2,4'-thieno[3,2-e][1,2]thiazin], 1',1'-dioxide of example 6 with a yield of 89%.

General Procedure 5

Hydrolisis of the Protective Group

The compound of formula 5 is dissolved in toluene (10-20 volumes) and an aqueous solution of hydrochloric acid 2-12 N is added. The mixture is stirred at a temperature which can vary between 20° C. and 80° C. for a time between 2 and 16 ore, until complete hydrolysis. The phases are separated and the product 1 is isolated through distillation of the organic solvent under vacuum, obtaining a solid with a HPLC assay of 85-95% and a yield of 65-99%.

Example 9

4H-thieno[3,2-e]-1,2-thiazin-4-one, 2,3-dihydro-, 1,1-dioxide 1 (X and R=hydrogen)

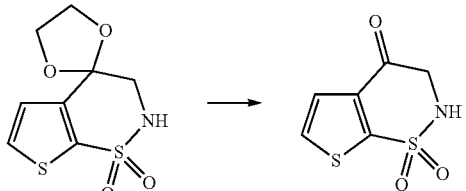

The desired compound is prepared according to the general procedure 5 starting from 2',3'-dihydrospiro[1,3-dioxolan-2,4'-thieno[3,2-e][1,2]thiazin], 1',1'-dioxide of example 3 with a yield of 66%.

$^1$H-NMR (300 MHz, DMSO-d$_6$): 8.90 (bt, 1H), 7.98 (d, 1H), 7.46 (d, 1H), 4.23 (d, 2H).

LC-MS: [M+H]$^+$=204.

Example 10

4H-thieno[3,2-e]-1,2-thiazin-4-one, 6-chloro 2,3-dihydro-, 1,1-dioxide 1 (X=chlorine and R=hydrogen)

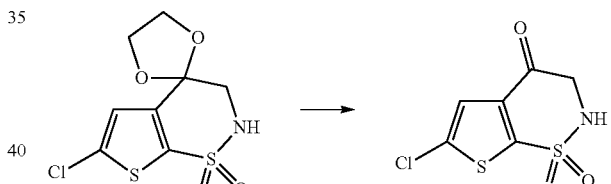

The desired compound is prepared according to general procedure 5 starting from 6'-chloro-2',3'-dihydrospiro[1,3-dioxolan-2,4'-thieno[3,2-e][1,2]thiazin], 1',1'-dioxide of example 4 with a yield of 95%.

$^1$H-NMR (300 MHz, DMSO-d$_6$): 9.08 (bs, 1H), 7.56 (s, 1H), 4.26 (d, 2H).

GC-MS: [M]$^{+\bullet}$=237.

Example 11

4H-thieno[3,2-e]-1,2-thiazin-4-one, 2,3-dihydro-2-(3-methoxypropyl)-, 1,1-dioxide 5 (X=hydrogen)

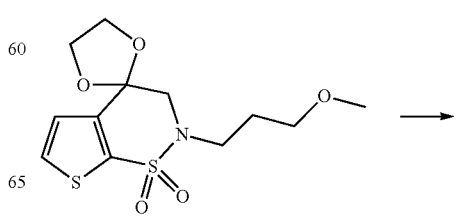

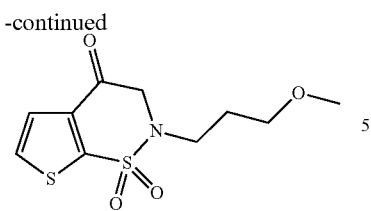

The desired compound is prepared according to the general procedure 5 starting from 2'-(3-methoxypropyl)-2',3'-dihydrospiro[1,3-dioxolan-2,4'-thieno[3,2-e][1,2]thiazin], 1',1'-dioxide of example 5 with a yield of 97%.

$^1$H-NMR (300 MHz, DMSO-d$_6$): 8.05 (d, 1H), 7.49 (m, 1H), 4.58 (s, 2H), 3.3-3.1 (m, 7H), 1.73 (m, 2H).

LC-MS: [M+H]$^+$=276.

Example 12

4H-thieno[3,2-e]-1,2-thiazin-4-one, 6-chloro 2,3-dihydro-2-(3-methoxypropyl)-, 1,1-dioxide 5 (X=chlorine)

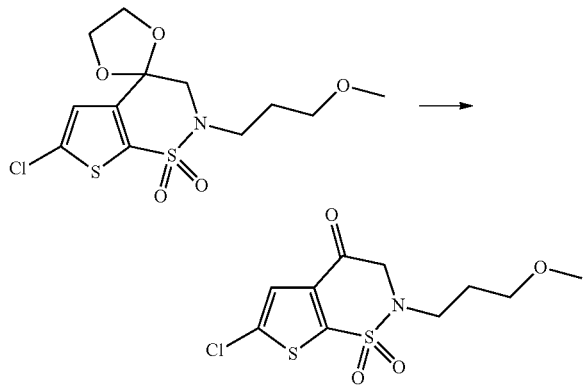

The desired compound is prepared according to the general procedure 5 starting from 6'-chloro-2'-(3-methoxypropyl)-2',3'-dihydrospiro[1,3-dioxolan-2,4'-thieno[3,2-e][1,2]thiazin], 1',1'-dioxide of example 6 with a yield of 99%.

$^1$H-NMR (300 MHz, DMSO-d$_6$): 7.59 (s, 1H), 4.50 (s, 2H), 3.3-3.2 (m, 4H), 3.18 (s, 3H), 1.74 (m, 2H).

LC-MS: [M+H]$^+$=310.

Example 13

2H-thieno[3,2-e]-1,2-thiazin-6-sulphonamide, 3,4-dihydro-2-(3-methoxypropyl)-4-oxo-, 1,1-dioxide 5 (X=Sulphonamide)

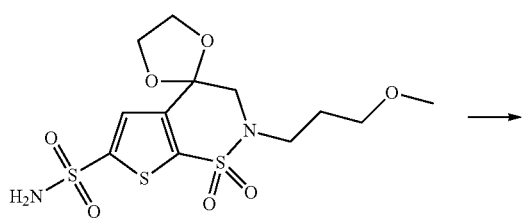

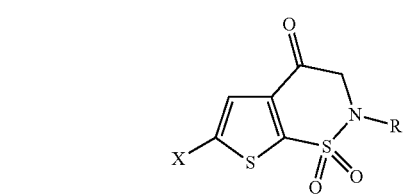

The desired compound is prepared according to the general procedure 5 starting from 2'-(3-methoxypropyl)-2',3'-dihydrospiro[1,3-dioxolan-2,4'-thieno[3,2-e][1,2]thiazin]-6'-sulphonamide, 1',1'-dioxide of examples 7 or 8 with a quantitative yield.

$^1$H-NMR (300 MHz, DMSO-d$_6$): 8.20 (s, 2H), 7.77 (s, 1H), 4.54 (s, 2H), 3.4-3.1 (m, 7H), 1.78 (m, 2H).

LC-MS: [M+H]$^+$=355.

The invention claimed is:
1. A process for the preparation of compounds of formula 1

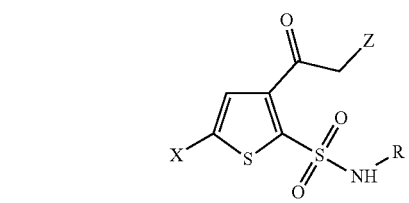

wherein X is hydrogen, halogen, thiol, thioether, or amide of sulphonic acid or halide of sulphonic acid,
R is hydrogen, alkyl, alkoxyalkyl, haloalkyl, aryl or arylalkyl, comprising the steps of
a) reaction of the compound of formula 2

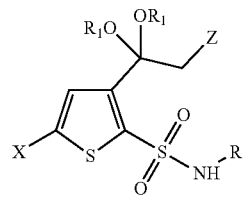

wherein X and R have the above mentioned meanings and Z is an halogen or a sulphonic ester,
with an alcohol or a diol to give the ketal of formula 3

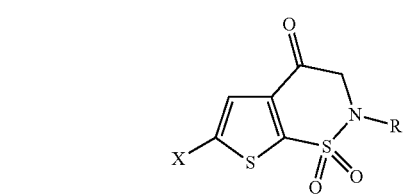

wherein X, R and Z have the above mentioned meaning and R$_1$ is an alkyl, linear or branched, or arylalkyl, and the two groups R$_1$ can be separated or joined to form a cycle, b) cyclization of the compound of formula 3 to form the compound of formula 4

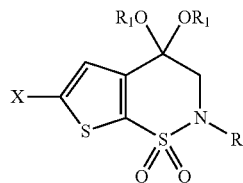

wherein X, R and $R_1$ have the above mentioned meaning,
c) hydrolysis of the compound of formula 4.

2. A process according to claim 1 where X is hydrogen, chlorine, bromine, sulphonamide.

3. A process according to claim 1 where R is hydrogen, 3-chloropropyl, 3-bromopropyl, 3-iodopropyl or 3-methoxypropyl.

4. A process according to claim 1 where Z is chlorine or bromine.

5. A process according to claim 1 where $R_1$ is methyl, ethyl, isopropyl, t-butyl, benzyl, or a chain formed by ethylene, propylene, 2,2-dimethylpropylene.

6. A process according to claim 1 comprising a step of transformation of the group X in a group X having a different meaning and/or transforming the group R in a group R with a different meaning after anyone of the steps a), b) or c).

7. A process according to claim 6 wherein, in the compounds of formula 3 or formula 4, X is hydrogen or chlorine, comprising the transformation of the group X into sulphonamide or a synthetic precursor thereof.

8. A process according to claim 6 wherein, in the compounds of formula 3 or formula 4, R is hydrogen, comprising the transformation of the group R in a group alkyl, alkoxyalkyl, haloalkyl, aryl or arylalkyl through a reaction with an alkyl halogenide, a sulphate, or a sulphonate.

9. A process according to claim 8 wherein the alkyl halogenide is 1,3-dichloropropane, 1,3-dibromopropane, 1,3-diiodopropane, 1-chloro-3-methoxypropane or 1-bromo-3-methoxypropane.

10. A process according to claim 6 wherein, in the compounds of formula 3 or formula 4, R is 3-chloropropyl, 3-bromopropyl, or 3-iodopropyl, comprising the transformation of the group R in 3-methoxypropyl through a reaction with sodium or potassium methylate, or with methanol in the presence of a strong base.

11. A process according to claim 6 for the preparation of 2-(3-methoxypropyl)-4-oxo-3,4-dihydro-2H-thieno[3,2-e][1,2]thiazin, 1,1-dioxide of formula 5

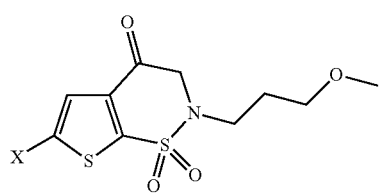

wherein X is hydrogen, chlorine, or sulphonamide, comprising the steps
a) reaction of the compound of formula 6

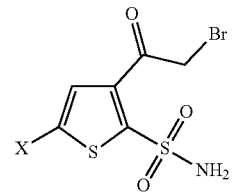

wherein X is hydrogen or chlorine,
with ethylene glycol in the presence of an acid, to obtain compound 7

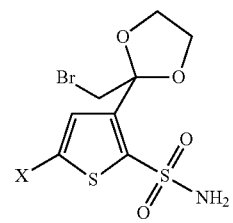

wherein X is hydrogen or chlorine,
b1) cyclization of the compound of formula 7 in the presence of a base to form the compound of formula 8

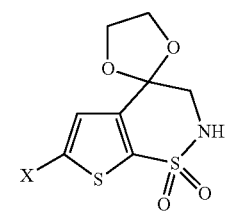

wherein X is hydrogen or chlorine;
b2) reaction of the compound of formula 8 with 1-chloro-3-methoxypropane or 1-bromo-3-metoxypropane to form the compound of formula 9

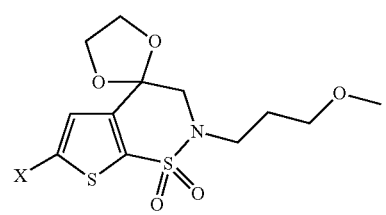

wherein X is hydrogen or chlorine;
b3) optional conversion of the group X into a sulphonamidic group;
c) hydrolysis of the compound of formula 9, wherein X is sulphonamide, hydrogen or chlorine.

12. A process for the preparation of Brinzolamide

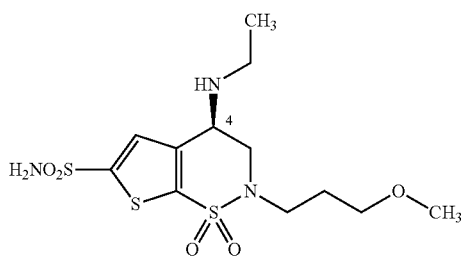 [SMILES: CCN[C@H]1CN(CCCOC)S(=O)(=O)c2sc(S(N)(=O)=O)cc21]

comprising the process of claim 1 and one or more of the following reactions:
  i. Reduction of the carbonyl in position 4 to an alcohol;
  ii. Stereoselective reduction of the carbonyl in position 4 to an alcohol;
  iii. Transformation of the alcohol in position 4 obtained at i and ii in halogenide or sulphonic ester;
  iv. Substitution of the halogenide or the sulphonic ester obtained at iii with an amine;
  v. Reaction of the ketone with an amine to form the ketimine in position 4;
  vi. Reduction of the ketimine in position 4 obtained at v to an amine;
  vii. Stereoselective reduction of the ketimine in position 4;
  viii. Transformation of the group X in a group X with a different meaning;
  ix. Transformation of the group R in a group R with a different meaning.
  x. Resolution of a racemate.

* * * * *